United States Patent
Khalaj

(10) Patent No.: US 10,898,679 B2
(45) Date of Patent: Jan. 26, 2021

(54) OVER-THE-NEEDLE CATHETER INSERT

(71) Applicant: Avent, Inc., Alpharetta, GA (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 47 days.

(21) Appl. No.: 16/284,038

(22) Filed: Feb. 25, 2019

(65) Prior Publication Data

US 2019/0184133 A1  Jun. 20, 2019

Related U.S. Application Data

(62) Division of application No. 14/306,625, filed on Jun. 17, 2014, now Pat. No. 10,252,026.

(51) Int. Cl.
*A61M 25/00* (2006.01)
*A61N 1/05* (2006.01)
(Continued)

(52) U.S. Cl.
CPC ...... *A61M 25/005* (2013.01); *A61M 25/0102* (2013.01); *A61M 25/0606* (2013.01);
(Continued)

(58) Field of Classification Search
CPC .. A61M 2025/0059; A61M 2025/0063; A61M 25/005; A61M 25/0102; A61M 25/0606; A61N 1/05; A61N 1/0551
See application file for complete search history.

(56) References Cited

U.S. PATENT DOCUMENTS 4,828,549 A   5/1989  Kvalo
4,966,586 A  10/1990  Vaillancourt
(Continued)

FOREIGN PATENT DOCUMENTS

WO   WO 2012/159000 A2   11/2012

OTHER PUBLICATIONS

International Search Report and Written Opinion for PCT/US2015/035050, dated Dec. 17, 2015, 19 pages.

*Primary Examiner* — Jason E Flick
(74) *Attorney, Agent, or Firm* — Dority & Manning, P.A.

(57) ABSTRACT

The present disclosure is directed to an over-the-needle (OTN) catheter assembly having a structural member configured therein. The OTN catheter assembly includes a catheter coaxially mounted onto a needle. In one embodiment, the structural member includes a coil insert that is embedded into an interior wall of the catheter, thereby preventing kinking of the catheter when being inserted within a patient. In another embodiment, the structural member may be a separate and removable coil insert that is inserted into the catheter after the OTN catheter assembly has been placed in a targeted site within the patient and the needle is removed. In a further embodiment, the structural member may be a separate and removable solid insert having a blunt distal end that is inserted into the catheter after the OTN catheter assembly has been placed in a targeted site within the patient and the needle is removed. Thus, the structural member is capable of advancing the catheter to one or more targeted sites within the patient, if desired, without causing further discomfort to the patient.

5 Claims, 7 Drawing Sheets

(51) Int. Cl.
*A61M 25/06* (2006.01)
*A61M 25/01* (2006.01)

(52) U.S. Cl.
CPC ....... *A61N 1/05* (2013.01); *A61M 2025/0059* (2013.01); *A61M 2025/0063* (2013.01); *A61N 1/0551* (2013.01)

(56) References Cited

U.S. PATENT DOCUMENTS

| | | |
|---|---|---|
| 4,985,022 A | 1/1991 | Fearnot et al. |
| 5,573,520 A | 11/1996 | Schwartz et al. |
| 5,807,395 A | 9/1998 | Mulier et al. |
| 5,935,108 A | 8/1999 | Katoh et al. |
| 8,303,570 B2 | 11/2012 | Gregorich et al. |
| 8,611,993 B2 | 12/2013 | Vitullo et al. |
| 8,641,677 B2 | 2/2014 | Rawls |
| 8,986,283 B2 | 3/2015 | Rajendran et al. |
| 2008/0287917 A1 | 11/2008 | Cunningham |
| 2009/0287189 A1 | 11/2009 | Suwito |
| 2011/0178464 A1 | 7/2011 | Rawls |
| 2012/0078095 A1 | 3/2012 | Heck |
| 2014/0025039 A1* | 1/2014 | Rajendran ............ A61M 19/00 604/512 |

\* cited by examiner

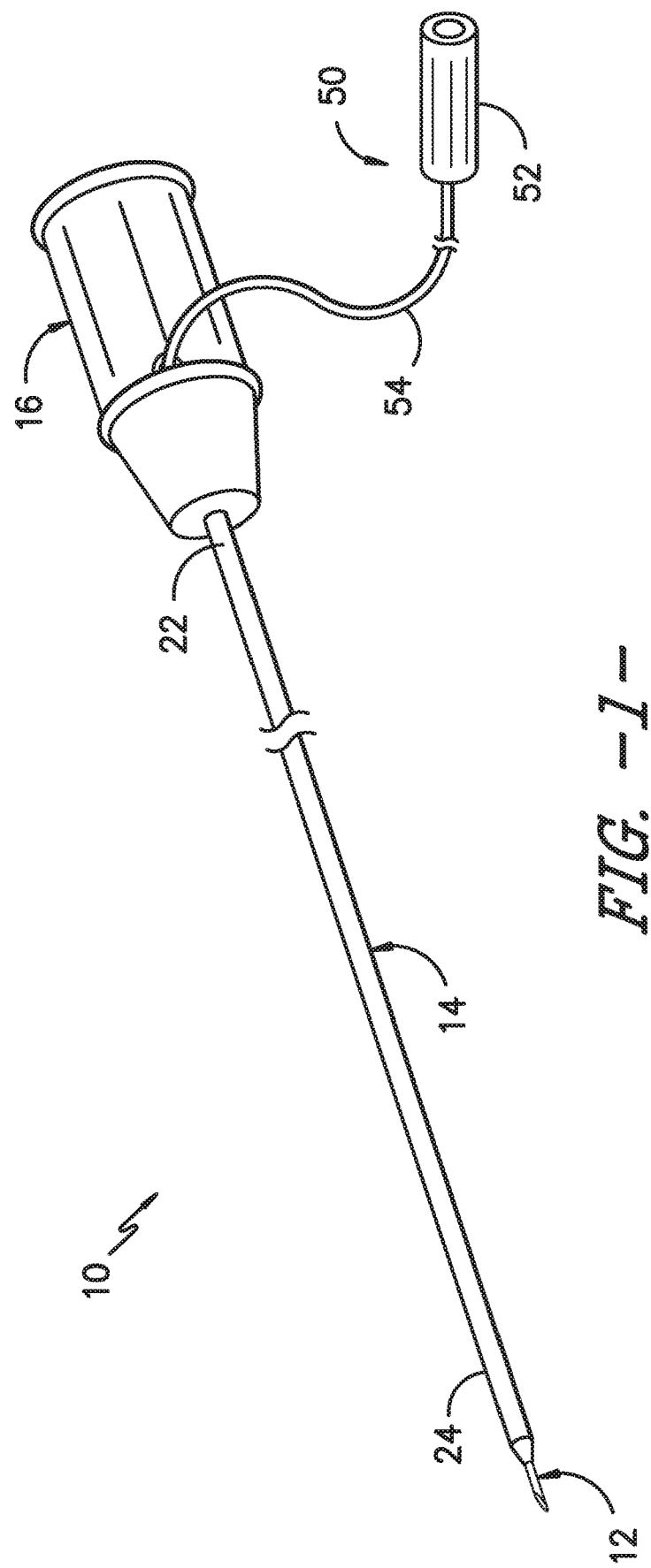
FIG. -1-

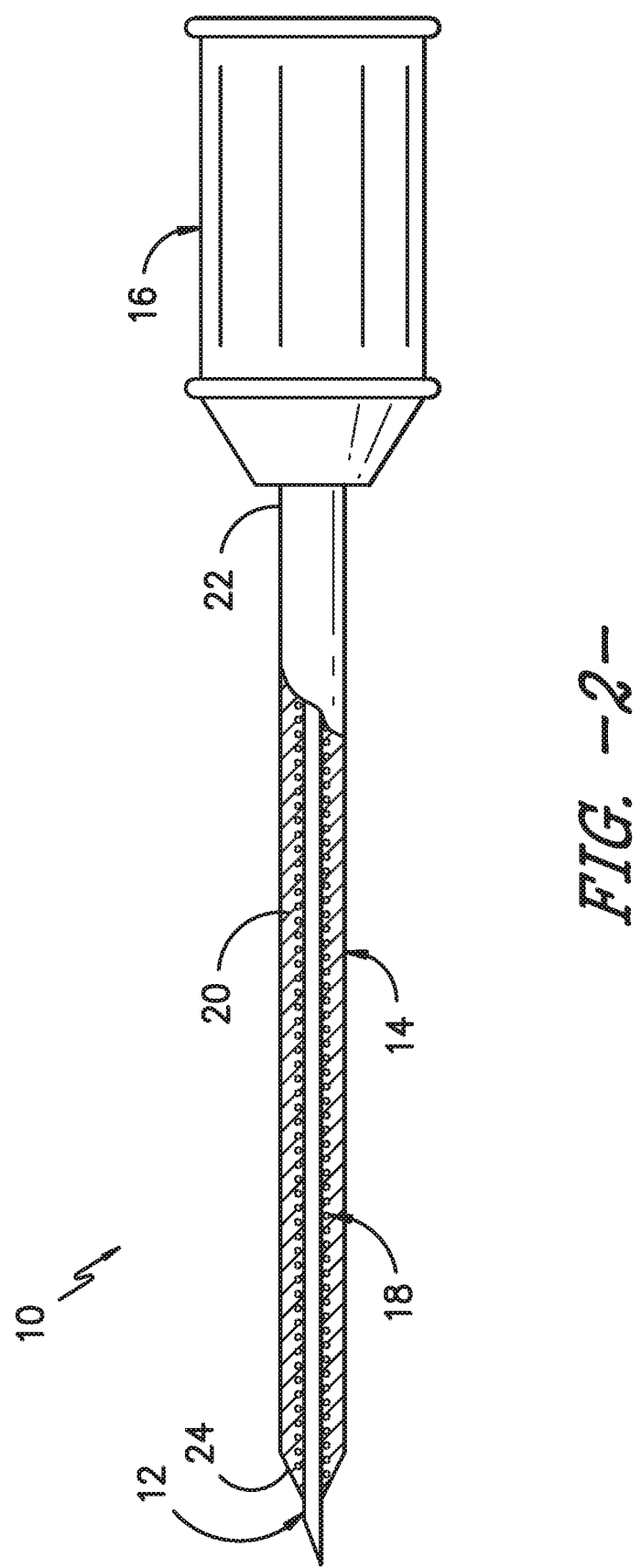
FIG. -2-

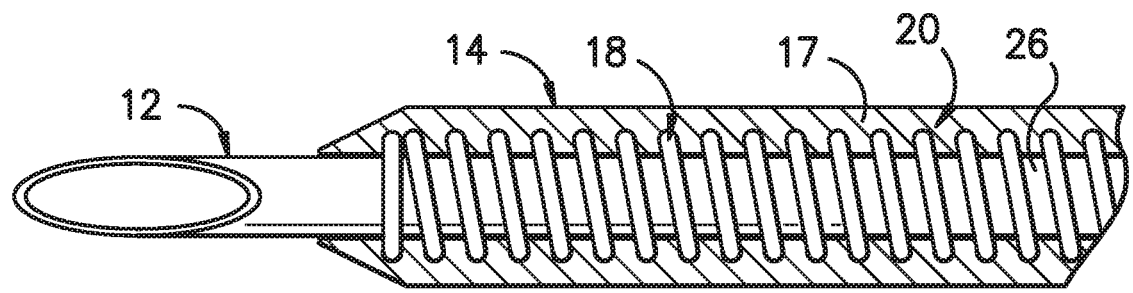
FIG. -3-
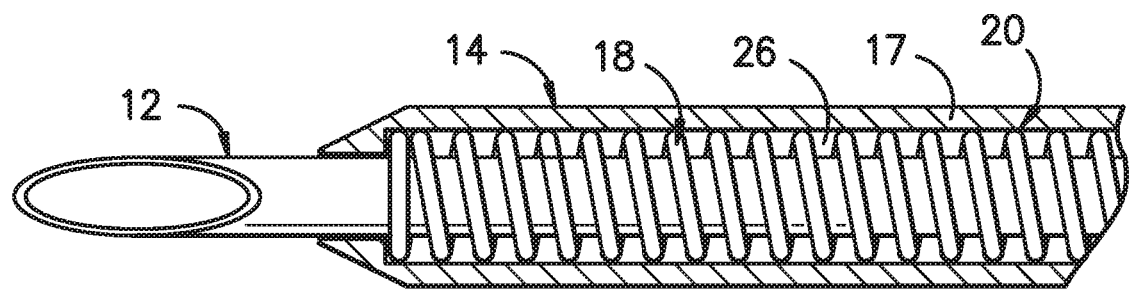
FIG. -4-

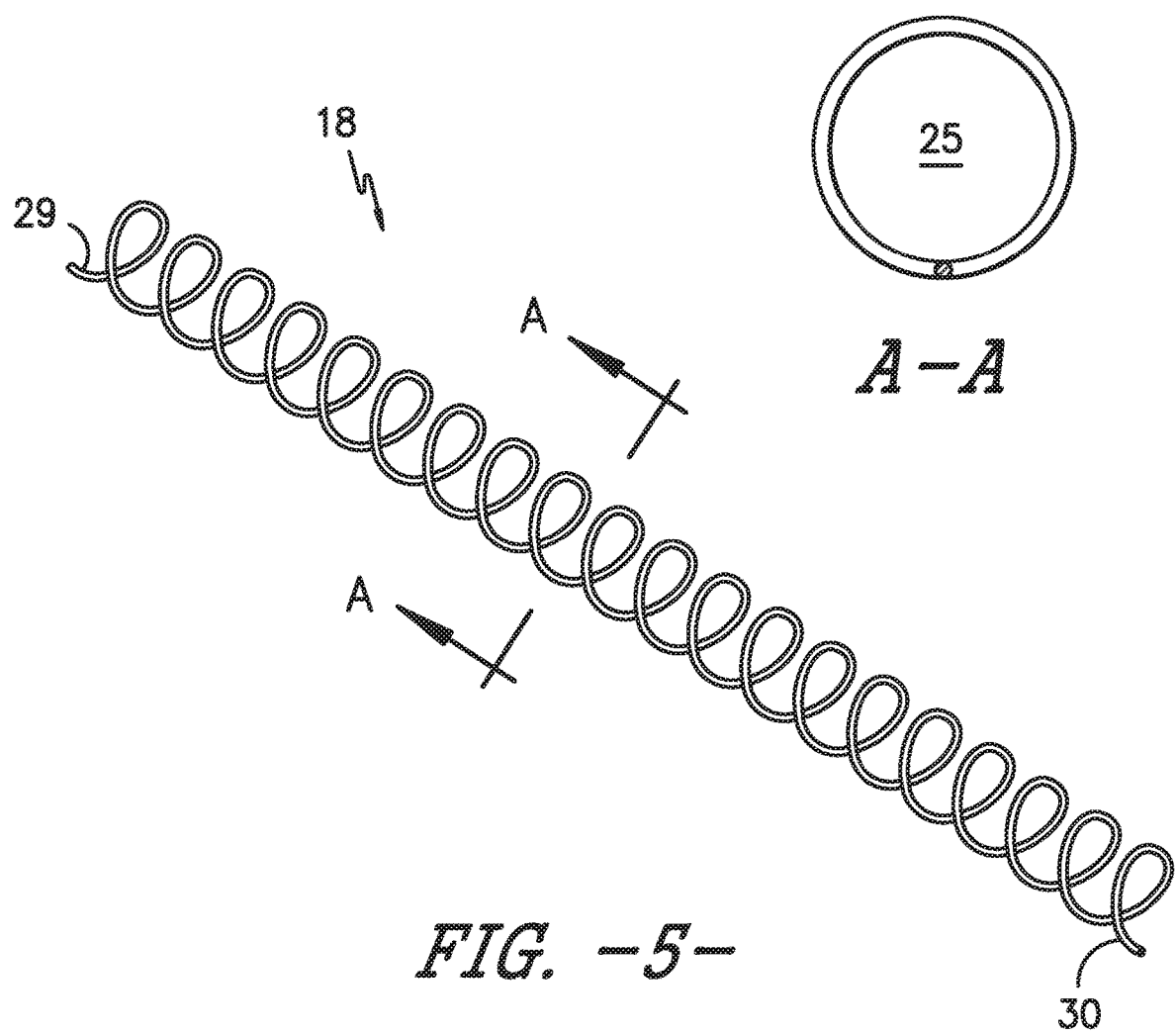
FIG. -5-

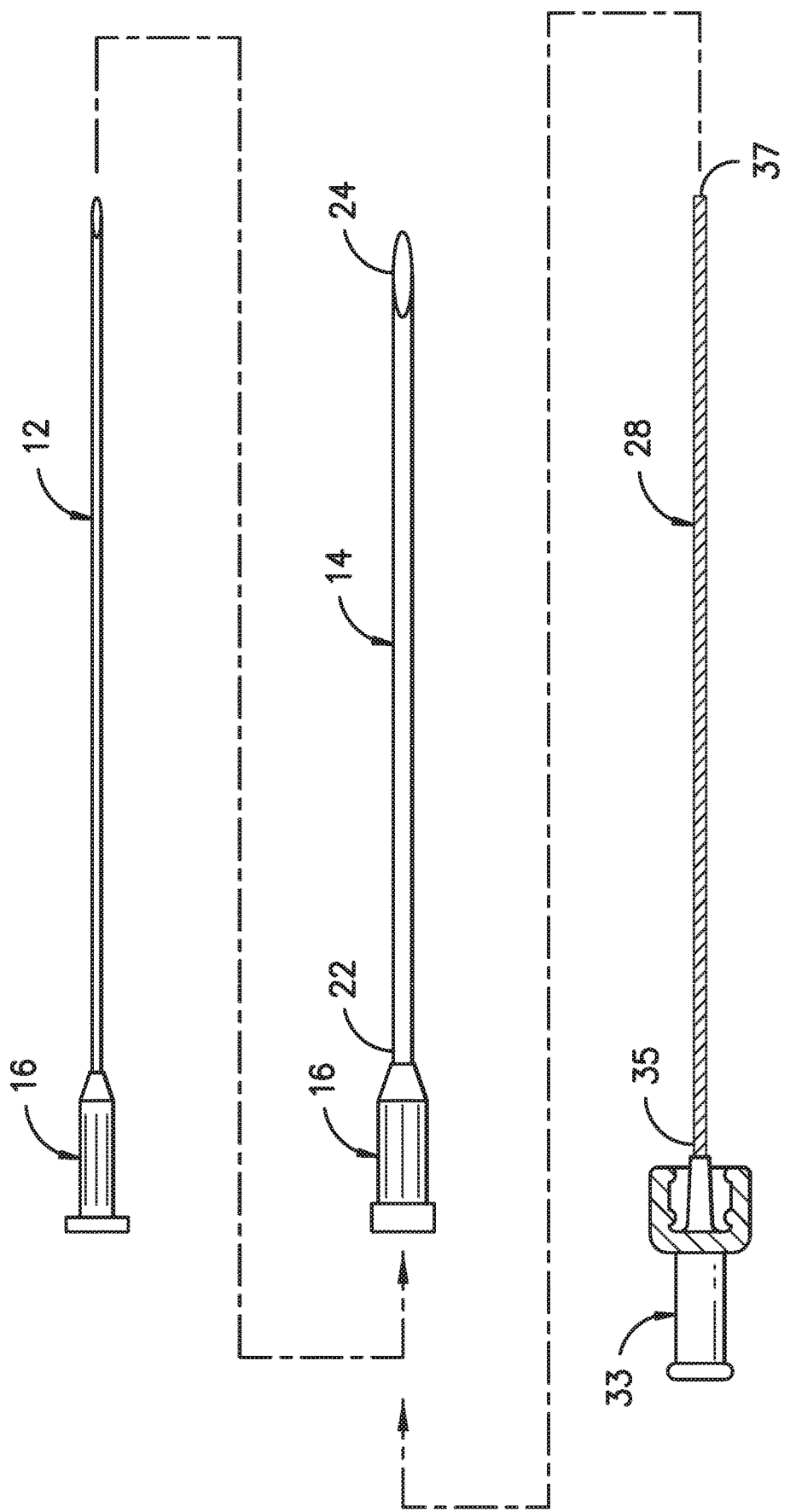
FIG. -6-

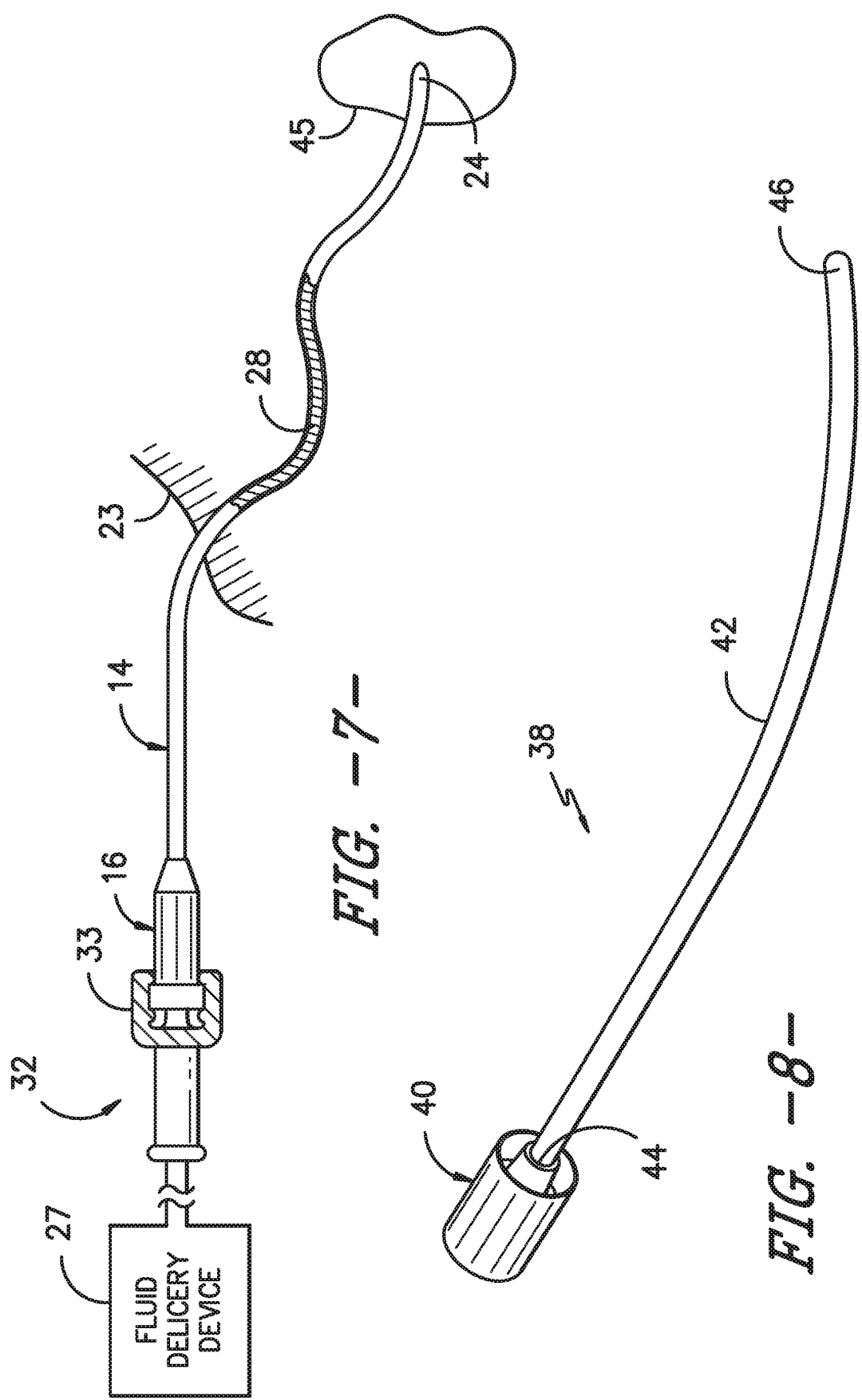

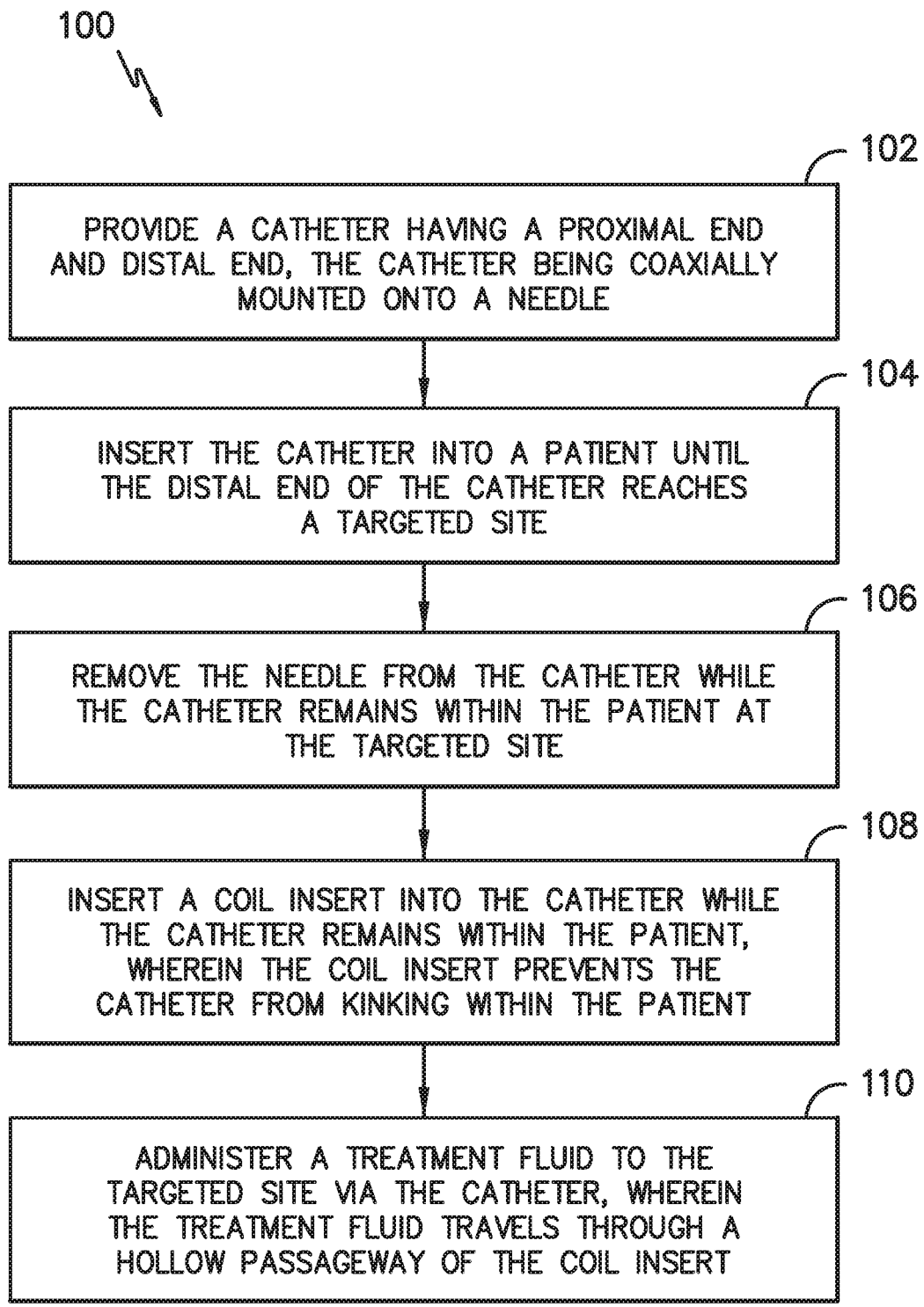
FIG. -9-

OVER-THE-NEEDLE CATHETER INSERT

RELATED APPLICATION

The present application is a divisional of U.S. application Ser. No. 14/306,625, filed on Jun. 17, 2014, which is incorporated herein in its entirety by reference hereto.

FIELD OF THE INVENTION

The present invention relates generally to the field of medical catheters and more particularly to over-the-needle (OTN) catheters.

BACKGROUND

Devices used to administer a fluid inside the anatomy of a patient are well known. For example, hypodermic needles, catheters, and the like are often used to deliver medication and other fluids to targeted sites within the body. In many instances, catheters are preferred because they can deliver fluid to a particular site over a period of time. Since catheters are generally made of a flexible plastic material, a needle is typically used to insert the catheter within a patient. For example, certain catheters, generally referred to as "through-the-needle" catheters, often require stiff, hollow introducer needles for placement within the anatomy. Thus, the catheter can be inserted through the needle after the needle is located at the targeted site. Typically, such introducer needles have sharp tips that may damage tissue and/or nerves during their delivery into a body, thus causing discomfort for the patient.

Another type of catheters, generally referred to as "over-the-needle" (OTN) catheters, include a catheter coaxially mounted onto a needle. In this type of catheter, the catheter and the needle may be inserted into a patient together. Once the catheter and the needle are located at the targeted site, the needle can be removed, leaving the catheter in place. Thus, OTN catheters can be purposely directed to an exact location without the need to thread the catheter within a patient. Accordingly, OTN catheters have gained increased attention in regard to delivering anesthetic medication, for example, for the purposes of nerve block. In order for OTN catheters to properly deliver fluids into the anatomy of a patient while also minimizing discomfort, the catheters should be designed to have the thinnest walls possible without being susceptible to kinking when being inserted within a patient.

As such, the medical art is continuously seeking new and improved OTN catheters that are not susceptible to kinking when being inserted into a patient. Accordingly, the present invention is directed to an OTN catheter assembly that addresses the aforementioned problems.

SUMMARY OF THE INVENTION

Objects and advantages of the invention will be set forth in part in the following description, or may be obvious from the description, or may be learned through practice of the invention.

In certain aspects, the present invention relates to an over-the-needle (OTN) catheter assembly. The OTN catheter assembly includes a catheter having a body with a proximal end and a distal end coaxially mounted over a needle and a coil insert. The body of the catheter defines a lumen extending from the proximal end to the distal end. The coil insert is configured within at least a portion of the lumen and includes a first end and second end. Further, the coil insert defines a hollow passageway extending from the first end to the second end. The needle is configured within the hollow passageway of the coil insert. Thus, the coil insert prevents the catheter from kinking when the catheter is within a patient.

In one embodiment, the coil insert is molded or embedded into an interior wall of the body of the catheter. In another embodiment, the OTN catheter assembly further includes a hub configured with the proximal end of the catheter. Further, in an additional embodiment, the coil insert may further include a handle configured to engage the hub of the catheter so as to form a hub assembly. In certain embodiments, the hub assembly may be configured to engage a fluid delivery device.

In a further embodiment, the coil insert includes a conductive material, e.g. a metal. Thus, in one embodiment, the OTN catheter assembly may include a stimulation assembly configured with the coil insert that is configured to provide stimulation to a targeted site within the patient.

In another aspect, the present invention relates to an over-the-needle (OTN) catheter assembly. The OTN catheter assembly includes a catheter having a body with a proximal end and a distal end coaxially mounted over a needle and a structural member. The body of the catheter defines a lumen extending from the proximal end to the distal end. The needle is configured to fit within at least a portion of the lumen so as to guide the catheter within a patient to a targeted site. The structural member is configured to fit within at least a portion of the lumen after the catheter is placed adjacent to the targeted site and the needle is removed, wherein the structural member prevents the catheter from kinking when the catheter is within the patient.

In one embodiment, the structural member includes a conductive coil insert. In another embodiment, the catheter may have a first length, whereas the conductive coil insert may include a second length that is longer than the first length such that the conductive coil insert is configured to extend past the distal end of the catheter when inserted therethrough. In a further embodiment, the OTN catheter assembly may include a hub configured with the proximal end of the catheter. Similarly, the coil insert may include a handle configured to engage the hub of the catheter so as to form a hub assembly. Thus, in certain embodiments, the catheter assembly may also include a stimulation assembly configured with the hub assembly and the conductive coil insert so as to provide stimulation to the targeted site within the patient. In addition, as mentioned, in certain embodiments, the hub assembly may be configured to engage a fluid delivery device.

In another embodiment, the structural member includes a solid insert having a rounded distal end. Thus, in one embodiment, the structural member is also configured to advance the catheter within the patient.

In yet another aspect, the present invention relates to a method for using an over-the-needle (OTN) catheter assembly to provide treatment to a targeted site within a patient. The method includes providing a catheter having a proximal end and distal end that is coaxially mounted onto a needle. The method also includes inserting simultaneously the catheter into the patient until the distal end of the catheter reaches the targeted site. Another step includes removing the needle from the catheter while the catheter remains within the patient adjacent to the targeted site. After removing the needle, the method also includes inserting a coil insert into the catheter while the distal end of the catheter remains within the patient so as to prevent kinking within the patient. Another step includes administering a treatment fluid to the targeted site via the catheter, wherein the treatment fluid travels through a hollow passageway of the coil insert.

In one embodiment, the catheter further includes a hub configured with the proximal end of the catheter. In a further embodiment, the coil insert may include a handle configured to engage the hub of the catheter. Thus, in various embodiments, the method may include coupling the handle of the coil insert to the hub of the catheter so as to form a hub assembly that secures the coil insert in place.

In a further embodiment, the coil insert may include a conductive material, such as a metal wire coiled into a helical shape. Thus, in various embodiments, the method may further include inserting the conductive coil insert into the catheter while the distal end of the catheter remains within the patient until a distal end of the coil insert extends past the distal end of the catheter. Further, the method may include coupling a stimulation assembly with the conductive coil insert, wherein the stimulation assembly is configured to provide stimulation to the targeted site. In still further embodiments, the method may include connecting the hub assembly to a fluid delivery device, and delivering a fluid, via the fluid delivery device, to the targeted site.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an OTN catheter assembly in accordance with aspects of the invention;

FIG. 2 illustrates a cross-sectional view of one embodiment of an OTN catheter assembly in accordance with aspects of the invention;

FIG. 3 illustrates a detailed, cross-sectional view of the embodiment of FIG. 2;

FIG. 4 illustrates a detailed, cross-sectional view of another embodiment of and OTN catheter assembly in accordance with aspects of the invention;

FIG. 5 illustrates a perspective view of one embodiment of a coil insert for an OTN catheter assembly in accordance with aspects of the invention;

FIG. 6 illustrates various components of an OTN catheter assembly in accordance with aspects of the invention;

FIG. 7 illustrates a perspective view of one embodiment of an OTN catheter assembly within a patient in accordance with aspects of the invention;

FIG. 8 illustrates a perspective view of one embodiment of a structural member for an OTN catheter assembly in accordance with aspects of the invention; and FIG. 9 illustrates a flow diagram of one embodiment of a method for using an OTN catheter assembly to provide treatment to a targeted site within a patient in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components relative to each other and to the patient. "Distal" refers to the direction that is closest to the wound site (e.g., the distal end of the catheter is the end oriented towards a catheter insertion site), and "proximal" refers to the opposite direction (e.g., the proximal end of the catheter is typically inserted into a catheter connector, which in turn is typically connected to a fluid delivery device).

Generally, the present disclosure is directed to an over-the-needle (OTN) catheter assembly having a coil insert configured therein so as to prevent kinking of the catheter as it in being advanced towards a nerve bundle within a patient. Thus, the OTN catheter assembly of the present disclosure is particularly useful for delivery anesthetic medication to the nerve bundle to provide a nerve block during a medical procedure. In various embodiments, the OTN catheter assembly includes a catheter coaxially mounted onto a needle. More specifically, the catheter may also include a coil insert embedded into an interior wall thereof. Thus, the coil insert provides an OTN catheter assembly that is capable of having thin walls without being susceptible to kinking when being inserted within a patient. In another embodiment, the coil insert may be a separate, removable insert that is inserted into the catheter after the catheter assembly is placed at a targeted site within the patient and the needle is removed. Thus, the coil insert is capable of advancing the catheter within the patient, if desired, without causing further discomfort to the patient.

Referring now to the drawings, various views of one embodiment of an over-the-needle (OTN) catheter assembly 10 according to the present disclosure are illustrated in FIGS. 1-3. As shown, the catheter assembly 10 includes catheter 14 having a body 20 having a proximal end 22 and distal end 24 coaxially mounted onto a needle 12. In certain embodiments, the proximal end 22 may include a hub 16 configured thereon for mating communication with a fluid delivery device (not shown). As mentioned, the fluid delivery device may be any suitable device known in the art, such as a pump, reservoir, syringe, or the like. Further, the hub 16 may have any conventional configuration, such as a Luer-lock fitting.

As shown in FIG. 3, the body 20 of the catheter 14 defines a lumen 26 extending from the proximal end 22 of the catheter 14 to the distal end 24. Further, a structural member 18 is configured within at least a portion of the lumen 26. Referring particularly to the embodiment of FIGS. 2-7, the structural member 18 corresponds to a coil insert. More specifically, FIG. 5 illustrates the coil insert 18 before it is either inserted into the catheter 14 or before it is embedded into a catheter wall 17. Further, as shown, the coil insert 18 includes a first end 29 and second end 30 and defines a hollow passageway 25 extending from the first end 29 to the second end 30. Thus, as shown in FIG. 3, the needle 12 can be configured within the hollow passageway 25 of the coil insert 18 and the assembly 10 can be simultaneously inserted into a patient. Accordingly, the coil insert 18 is configured to prevent the catheter 14 from kinking when being advanced to a targeted site within a patient.

In certain embodiments, as shown particularly in FIGS. 2 and 3, the coil insert 18 may be molded or embedded into an interior wall of the body 20 of the catheter 14. For example, as shown in FIG. 3, the coil insert 18 may be partially embedded into the catheter wall 17 so as to provide a flexible, yet durable catheter 14. Thus, the OTN catheter assembly 10 can be designed with thin walls that are kink-resistant so as to minimize discomfort to a patient while also efficiently delivering fluids to a targeted site of a patient.

In additional embodiments, as shown in FIG. 1, the OTN catheter assembly 10 may also include a stimulation assembly 50 configured with the coil insert 18 and/or the needle 12. Thus, in certain embodiments, the stimulation assembly 50 is configured to provide stimulation to the targeted site within the patient via the coil insert 18. More specifically, the stimulation assembly 50 may include a stimulator connector 52 and a stimulation wire 54 configured with the coil insert 18. It should be understood that the stimulation assembly 50 can be any suitable assembly known in the art and the illustrated embodiment is provided for illustrative purposes only.

In alternative embodiments, as shown in FIGS. 4, 6, and 7, the structural member may be a separate, removable coil insert 28 that can be inserted within the catheter 14 rather than molded or embedded into the catheter walls. More specifically, as shown in FIG. 6, the coil insert 28 may include a flexible, yet rigid spring coil that extends from a first end 35 to a second end 37 so as to define a length. In one embodiment, the length of the coil insert 28 may be shorter than the catheter 14. In another embodiment, the length of the coil insert 28 may be approximately equal to the length of the catheter 14. In still further embodiments, the length of the coil insert 28 may be longer than that of the catheter 14 so as to extend past the distal end 24 of the catheter 14 when inserted therethrough. In such embodiments, the coil insert 18 may also include a wire such that a user can provide stimulation through the coil insert 18 to a targeted site to ensure that the catheter 14 is properly located (e.g. near the nerve bundle) even after the needle 12 is removed from the catheter 14.

In additional embodiments, the coil insert 28 may have a handle 33 mounted onto the first end 35 of the coil insert 28 to assist a user with inserting and/or removing the coil insert 28 into or out of the catheter 14. In addition, the handle 33 of the coil insert 28 may be configured to engage the hub 16 of the catheter 14 so as to form a hub assembly 32. Thus, in certain embodiments, the hub assembly 32 may be configured to engage a fluid delivery device 27 as described herein.

The OTN catheter assembly 10 as described herein provides a catheter 14 having a smaller-than-average diameter due to the thin wall 17 that also prevents the catheter 14 from kinking when placed within a patient. More specifically, as shown in the embodiment of FIG. 6, the needle 12 is first placed inside the catheter 14 such that the catheter 14 is coaxially mounted onto the needle 12 to form the OTN catheter assembly 10. The catheter 14 and the needle can then be simultaneously inserted into a patient's body 45 until a distal end of the catheter 14 reaches a targeted site 45 (FIG. 7). Once at the targeted site 45, the needle 12 is removed from the patient, leaving the catheter 14 in place. After removing the needle 12, the coil insert 28 can be inserted into the catheter 14 and locked into place using the hub assembly 32. The hub assembly 32 may then be connected to a fluid delivery device 27 such that a fluid, e.g. a medicine, flows through the catheter 14 with the coil insert 28 inserted therethrough to the targeted site 45 within the patient's body 23.

Referring now to FIG. 8, another embodiment of a structural member 38 for an OTN catheter assembly 10 according to the present disclosure is illustrated. As shown, the structural member 38 corresponds to a solid insert 42 having a proximal end 44 and rounded or blunt distal end 46. As shown, the proximal end 44 may also include a hub 40. Thus, the solid insert 42 is configured to assist with advancing the catheter 14 within a patient, e.g. to another targeted site, without causing further damage and/or discomfort to the patient.

It should also be understood that the structural member(s) 18, 28, 38 as described herein may be constructed of any suitable material. For example, in certain embodiments, the structural member that corresponds to coil inserts 18 and 28 may be constructed of a flexible, conductive material formed into the shape of helix so as not to restrict flow within the catheter 14. More specifically, the coil insert 18 may be constructed of aluminum, copper, stainless steel, or any other suitable metal or metal composite material. In alternative embodiments, the structural member that corresponds to the solid insert 38 may be formed of a material that is rigid enough to keep its shape, yet flexible enough to curve with the shape of the catheter 14 when inserted into a patient. For example, the solid insert 38 may constructed of a flexible material, such as plastic, rubber, a polymeric material, silicone, an elastomeric material, or any other suitable material. More specifically, in various embodiments, the structural member may be constructed of polyisoprene, polyurethane, styrene butadiene, and/or any other suitable flexible material.

Referring now to FIG. 9, a flow diagram of one embodiment of a method 100 for using an over-the-needle catheter assembly to provide treatment to a targeted site within a patient is illustrated. As shown in the illustrated embodiment, the method 100 includes a step 102 of providing a catheter having a proximal end and distal end that is coaxially mounted onto a needle. Another step 104 includes inserting the catheter and the needle simultaneously into a patient until the distal end of the catheter reaches a targeted site. The method 100 also includes a step 106 of removing the needle from the catheter while the catheter remains within the patient adjacent to the targeted site. After removing the needle, a next step 108 includes inserting a coil insert into the catheter while the catheter remains within the patient, wherein the coil insert prevents the catheter from kinking within the patient. Another step 110 includes administering a treatment fluid to the targeted site via the catheter, wherein the treatment fluid travels through a hollow passageway of the coil insert. In additional embodiments, the method 100 may also include the step of coupling a handle of the coil insert to a hub of the catheter so as to form a hub assembly that secures the coil insert in place. In addition, the method 100 may include connecting the hub assembly to a fluid delivery device, and delivering a fluid, via the fluid delivery device, to the targeted site.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method for using an over-the-needle catheter assembly to provide treatment to a targeted site within a patient, the method comprising:
   providing a catheter having a proximal end and distal end, the catheter coaxially mounted onto a needle, the proximal end of the catheter comprising a hub;
   inserting simultaneously the catheter and the needle into the patient until the distal end of the catheter reaches the targeted site;
   removing the needle from the catheter while the catheter remains within the patient adjacent to the targeted site;
   after removing the needle, inserting a coil insert into the catheter while the distal end of the catheter remains within the patient, wherein the coil insert prevents the catheter from kinking within the patient, the coil insert comprising a handle comprising a central protrusion and an outer annular wall with an annular recess defined between the central protrusion and the outer annular wall, the outer annular wall comprising at least one rib;
   inserting the hub within the annular recess until a flange of the hub is secured in lace via the at least one rib so as to secure the hub and the handle together to form a hub assembly; and
   administering a treatment fluid to the targeted site via the catheter, wherein the treatment fluid travels through a hollow passageway of the coil insert.

2. The method of claim 1, wherein the coil insert is constructed of a conductive material.

3. The method of claim 2, further comprising inserting the conductive coil insert into the catheter while the distal end of the catheter remains within the patient until a distal end of the coil insert extends past the distal end of the catheter.

4. The method of claim 3, further comprising coupling a stimulation assembly with the conductive coil insert and providing stimulation to the targeted site via the stimulation assembly.

5. The method of claim 1, further comprising connecting the hub assembly to a fluid delivery device and delivering a fluid to the targeted site via the fluid delivery device.

* * * * *